United States Patent
Truitt et al.

(10) Patent No.: US 7,165,547 B2
(45) Date of Patent: *Jan. 23, 2007

(54) APPARATUS AND METHOD FOR PROVIDING HIGH FREQUENCY VARIABLE PRESSURE TO A PATIENT

(75) Inventors: Patrick W. Truitt, Pittsburgh, PA (US); William A. Truschel, Monroeville, PA (US); Bernie F. Hete, Trafford, PA (US); Michael Bobeck, Sarver, PA (US); Michael W. Haas, Trafford, PA (US)

(73) Assignee: RIC Investments, LLC, Wilmington, DE (US)

( * ) Notice: Subject to any disclaimer, the term of this patent is extended or adjusted under 35 U.S.C. 154(b) by 117 days.

This patent is subject to a terminal disclaimer.

(21) Appl. No.: 10/435,807

(22) Filed: May 12, 2003

(65) Prior Publication Data
US 2003/0192545 A1 Oct. 16, 2003

Related U.S. Application Data

(62) Division of application No. 09/665,280, filed on Sep. 20, 2000, now Pat. No. 6,581,596.

(60) Provisional application No. 60/156,295, filed on Sep. 24, 1999.

(51) Int. Cl.
*A61M 16/00* (2006.01)

(52) U.S. Cl. .......................... 128/204.21; 128/204.19; 128/204.23; 128/205.24

(58) Field of Classification Search ........... 128/204.18, 128/204.21, 205.24, 911, 205.18, 205.21, 128/204.19, 204.23; 137/908
See application file for complete search history.

(56) References Cited

U.S. PATENT DOCUMENTS

| 4,171,697 | A | * | 10/1979 | Arion ..................... 128/205.24 |
| 4,351,329 | A |   | 9/1982  | Ellestad et al. |
| 4,646,733 | A | * | 3/1987  | Stroh et al. ............ 128/207.16 |
| 4,821,709 | A |   | 4/1989  | Jensen |
| 4,919,132 | A |   | 4/1990  | Miser |
| 4,944,306 | A |   | 7/1990  | Alvino |

(Continued)

FOREIGN PATENT DOCUMENTS

WO    WO 98/50095    * 11/1998

*Primary Examiner*—Michael J. Hayes
*Assistant Examiner*—Michael G. Mendoza
(74) *Attorney, Agent, or Firm*—Richard J. Coldren; Michael W. Haas; Timothy A. Nathan

(57) ABSTRACT

A high frequency pressure oscillation device that selective restricts the flow of breathing gas to or from a patient to produce pressure spikes in the patient's airway that facilitate clearing secretions from the patient's airway. The device includes a patient circuit that defines a closed path between a source of breathing gas and the patient's airway. A valve is disposed in the patient circuit such that in an open position the path between the source of breathing gas and the airway of the patient is substantially unobstructed. When the valve is in a closed position, the path between the source of breathing gas and the patient's airway is at least partially obstructed to create the pressure spikes. An actuating system associated with the valve alternatively places the valve in the open position and in the closed position at a predetermined oscillation rate that is independent of patient effort.

18 Claims, 9 Drawing Sheets

U.S. PATENT DOCUMENTS

| | | |
|---|---|---|
| 5,107,830 A | 4/1992 | Younes |
| 5,137,026 A | 8/1992 | Waterson et al. |
| 5,224,487 A | 7/1993 | Bellofatto et al. |
| 5,555,880 A | 9/1996 | Winter et al. |
| 5,746,199 A * | 5/1998 | Bayron et al. ......... 128/205.24 |
| 5,931,163 A | 8/1999 | Stegmann et al. |
| 6,041,780 A | 3/2000 | Richard et al. |
| 6,182,656 B1 | 2/2001 | Sagiv |
| 6,182,658 B1 * | 2/2001 | Hayek ................... 128/205.24 |
| 6,209,540 B1 * | 4/2001 | Sugiura et al. ........ 128/204.18 |
| 6,363,933 B1 | 4/2002 | Berthon-Jones |
| 6,435,182 B1 | 8/2002 | Lutchen et al. |
| 6,446,629 B1 * | 9/2002 | Takaki et al. .......... 128/204.18 |
| 6,694,976 B1 * | 2/2004 | Takaki et al. .......... 128/204.18 |
| 6,708,690 B1 * | 3/2004 | Hete et al. ............. 128/204.18 |

* cited by examiner

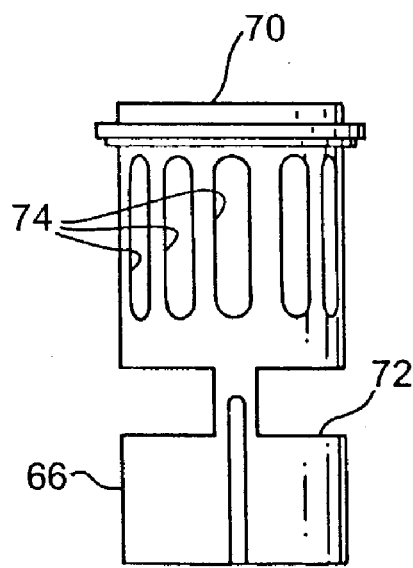 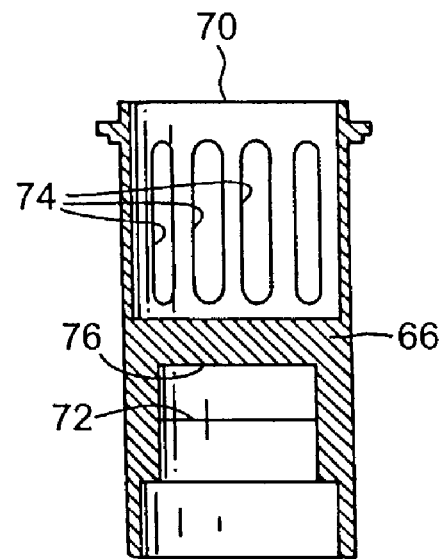
FIG. 3A  FIG. 3B
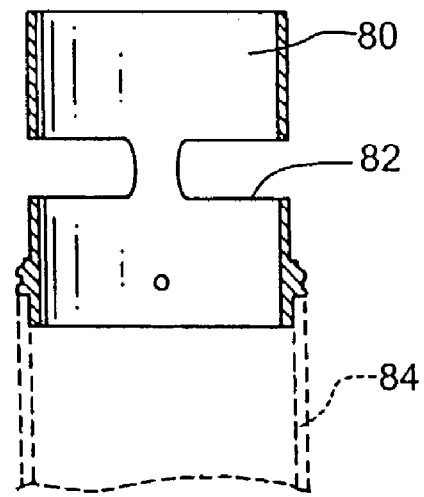
FIG. 4

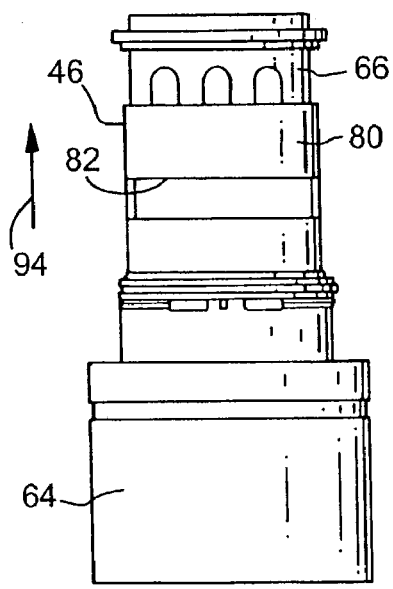
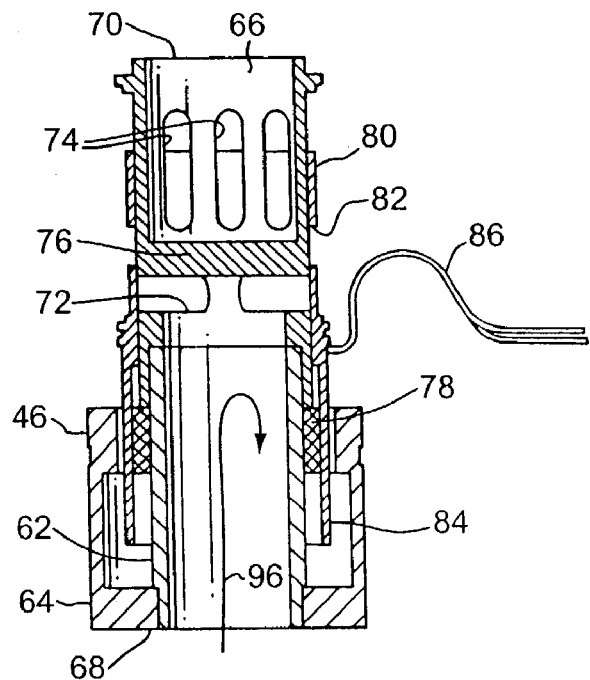
FIG. 5 A  FIG. 5B
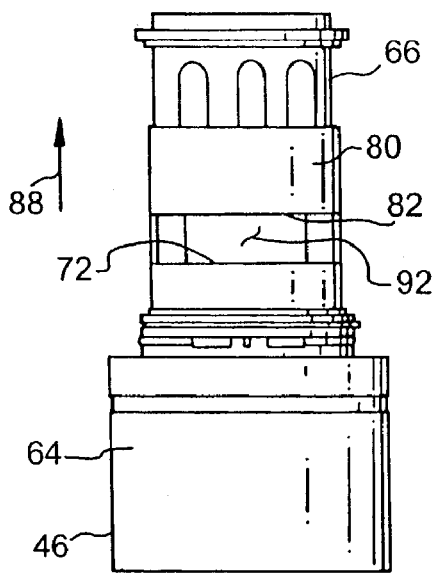
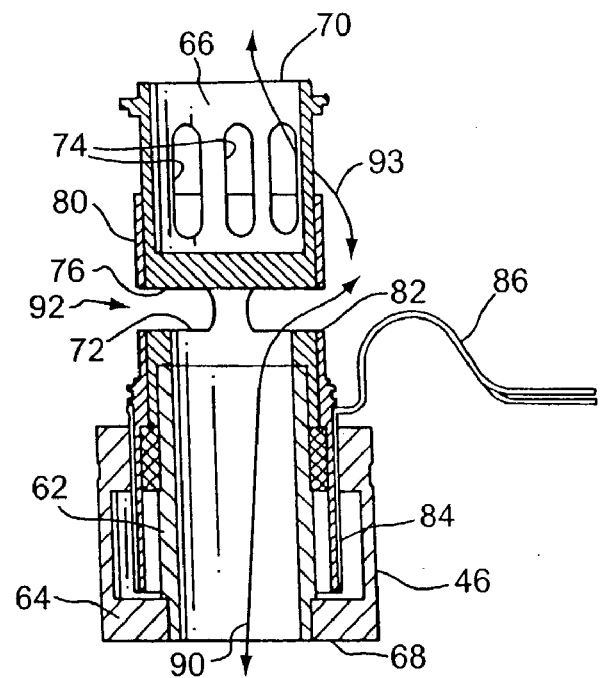
FIG. 6 A  FIG. 6B

APPARATUS AND METHOD FOR PROVIDING HIGH FREQUENCY VARIABLE PRESSURE TO A PATIENT

This application claims priority under 35 U.S.C. § 120 as a Divisional application from U.S. patent application Ser. No. 09/665,280 filed Sep. 20, 2000, now U.S. Pat. No. 6,581,596 which claims priority under 35 U.S.C. § 119(e) from U.S. provisional patent application No. 60/156,295 filed Sep. 24, 1999.

BACKGROUND OF THE INVENTION

1. Field of the Invention

The present invention pertains to an apparatus and method of providing high frequency variable pressures to an airway of a patient, and, in particular, to an apparatus and method of providing high frequency variable pressures in which a valve generates the pressure oscillations in the delivery of gas to or from the patient independent of patient effort.

2. Description of the Related Art

Many people have difficulty clearing secretions, such as mucous or fluids, from their respiratory system. In a healthy patient, accumulated secretions are removed from the respiratory system by clearing the throat or coughing. Some patients, however, such as those with a weakened respiratory system, may not be physically able to perform such a secretion clearing movement with sufficient strength to remove or loosen the secretion.

To address this problem, a device is known that creates an abrupt pressure variation in the patient's airway, particularly during exhalation, to assist in dislodging or removing the secretions. An example of such a device is a hand-held flutter valve, which uses a ball valve to create the pressure oscillations. When the patient breathes into the flutter valve, the force of the patient's exhalation moves a ball off a valve seat to open the valve. Gravity immediately urges the ball valve back onto the seat to obstruct the patient's expiratory flow until the expiratory force is sufficient to again urge the ball off of the seat. This process repeats as the patient exhales until the patient's expiratory force is not great enough to move the ball off of the seat. A series of pressure spikes occur in the patient's airway as a result of the temporary flow interruption caused by the closing and opening of the ball valve to facilitate loosening and removal of the patient's airway secretions.

There are disadvantages associated with this flutter valve secretion clearance device. For example, proper seating of the ball on the valve seat is only possible if the device is held in its upright position. Therefore, the conventional flutter valve device is very position sensitive. In addition, because the patient's own expiratory force is used to move the ball to the open position, the flutter valve cannot be used by patients with very weak respiratory systems who have very low expiratory flow rate.

Another device that provides pressure oscillations to the patient's airway is the Emerson Cough-a-Lator, produced by Emerson, Inc. This device provides both a positive and a negative pressure to the patient's airway to assist in secretion clearance. A mechanism in the device physically moves a portion of a patient circuit in a windshield wiper fashion between a first position, where a positive pressure output from a blower is coupled to the patient, and a second position, where a negative pressure at the input of the blower is coupled to the patient. This device is relatively large, complex, bulky and expensive, and, therefore, is not readily portable. It is also generally not convenient or easy to set up and use.

SUMMARY OF THE INVENTION

Accordingly, it is an object of the present invention to provide a high frequency pressure oscillation device and method that overcomes the shortcomings of conventional devices, such as the above-described flutter valve. This object is achieved according to one embodiment of the present invention by providing a high frequency pressure oscillation device that includes a patient circuit defining a closed path between a source of breathing gas and the airway of a patient. A valve in the patient circuit moves between an open position and a closed position. In the open position, the path between the source of breathing gas and the patient's airway is substantially unobstructed. In the closed position, the path between the source of breathing gas and the airway of the patient is at least partially obstructed so that the flow in the path is restricted. An actuating system alternatively places the valve in the open position and the closed position at a predetermined oscillation rate and does so independent of patient effort. Alternatively opening and closing, either completely or partially, the path between the patient's airway and the source of breathing gas while the patient inhales or exhales through that path generates pressure spikes in the patient's airway that facilitate loosening and removal of accumulated secretions.

It is yet another object of the present invention to provide a method of providing high frequency pressure oscillations to an airway of a patient that does not suffer from the disadvantages associated with conventional techniques. This object is achieved by providing a method that includes a) providing a patient circuit defining a closed path between a source of breathing gas and an airway of a patient, b) providing a valve in the patient circuit operable to control the flow of gas in the path, c) moving the valve to an open position within the patient circuit to substantially open the path between the source of breathing gas and the patient's airway, and d) moving the valve to at least a partially closed position within the patient circuit to restrict the path between the source of breathing gas and the patient's airway either completely or partially. According to the principles of the present invention, moving the valve between the open position and the closed position is accomplished independent of patient effort. Steps c) and d) are repeated to alternatively place the valve in the open and the closed positions at a predetermined oscillation rate. As noted above, alternatively opening and closing the path between the patient's airway and the source of breathing gas while the patient inhales or exhales through that path generates pressure spikes in the patient's airway that facilitates loosening and removal of accumulated secretions.

It is a further object of the present invention to provide the above-described secretion clearance device in combination with the functions of a conventional spirometer, so that a single device provides both a secretion clearance function and a pulmonary monitoring function. This object is achieved by providing the above-described secretion clearance device in combination with a pulmonary measurement system, such as a flow sensor, associated with the patient circuit. The pulmonary measurement system is capable of functioning as a spirometer that measures a characteristic associated with a pulmonary function of a patient, such as the rate of flow of gas through the patient circuit. In a further embodiment of the present invention, a mode selection switch is provided that allows a user to select between (1) the secretion clearance mode, in which the actuating system alternatively places the valve in the open position and the closed position at a predetermined oscillation rate to clear secretions from the airway as described above, and (2) a spirometer mode, in which the valve remains in the open position and the pulmonary measurement system measures a characteristic associated with a pulmonary function of a patient.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 3A and 3B are side and sectional views, respectively, of the barrel portion of the sleeve valve of FIGS. 1 and 2, with the barrel being rotated 90° in FIG. 3B from the position shown in FIG. 3A;

FIG. 4 is a sectional view of a sleeve portion of the sleeve valve of FIGS. 1 and 3;

FIGS. 5A and 5B are side and sectional views, respectively, of the sleeve valve of FIGS. 1 and 2 showing the valve in the closed position, with the valve being rotated 90° in FIG. 5B from the position shown in FIG. 5A;

FIGS. 6A and 6B are side and sectional views, respectively, of the sleeve valve of FIGS. 1 and 2 showing the valve in the open position, with the valve being rotated 90° in FIG. 6B from the position shown in FIG. 6A;

DETAILED DESCRIPTION OF THE PRESENTLY PREFERRED EMBODIMENTS OF THE INVENTION

Figure 1:
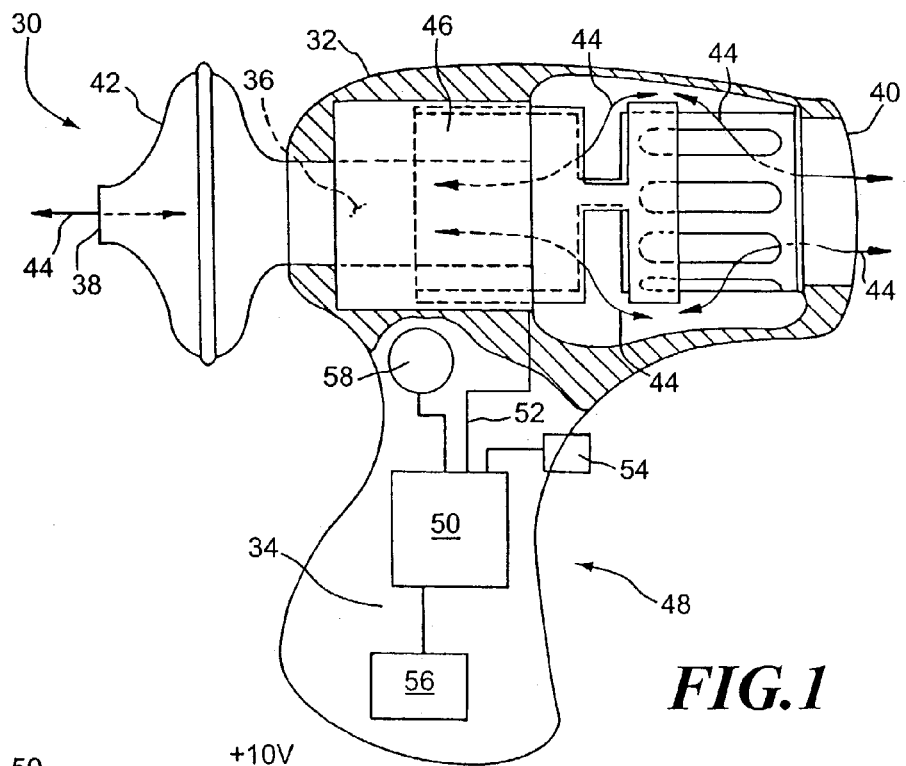
FIG. 1 is a side view, partially in section, of a high frequency pressure oscillation device according to the principles of the present invention.

FIG. 1 schematically illustrates a first exemplary embodiment of a high frequency pressure oscillation device 30 according to the principles of the present invention, and FIGS. 2–7 illustrate various components of that device. As shown in FIG. 1, high frequency pressure oscillation device 30 preferably includes a housing 32 having a handle 34 so that the device can be readily gripped by the user in one hand. A patient circuit 36 in the form of a conduit is defined in housing 32 between a patient end 38 and a breathing gas source end 40. In the illustrated exemplary embodiment, a mouthpiece 42, which preferably includes a bacteria filter, is removeably provided at patient end 38 so that the patient can breathe into patient circuit 36. Patient circuit 36 provides a path, as generally indicated by arrows 44, for the flow of gas between the patient and the breathing gas source, which in the illustrated embodiment is the ambient atmosphere.

A valve assembly 46 is provided in the patient circuit to control the flow of gas between the patient and the gas source. More specifically, valve assembly 46 preferably operates between two positions: (1) an open position in which path 44 between the source of breathing gas and the airway of a patient is substantially unobstructed, as shown in FIGS. 1, 5A and 5B, and (2) a closed position, in which path 44 between the source of breathing gas and the patient's airway is at least partially obstructed, thereby restricting the flow of gas in path 44. In the embodiment illustrated in FIGS. 1–6B, valve assembly 46 is a reciprocating sleeve valve, the details of which are provided below.

As the patient breathes into patient circuit 36 via mouthpiece 42, valve assembly 46 is actuated by an actuating system, generally indicated at 48, causing the valve to repeatedly open and close, which, in turn, repeatedly blocks and unblocks path 44. As the patient breathing into patient circuit 36, this abrupt blockage of path 44 from the patient to the source of breathing gas produces pressure spikes in the patient's airway that are conducive to clearing secretions from the airway. Actuating system 48 moves valve assembly 46 between the open position and the closed position independent of the flow of gas through patient circuit 36. That is, the means by which patient circuit 36 is repeatedly blocked and unblocked is not dependent on the effort of the patient, as is the case with the above-described conventional flutter valve. As a result, the pressure spikes are created in the patient's airway even if the patient is breathing into the patient circuit at very low flow rates. In addition, because actuating system 48 is not dependent on patient effort to move the valve between the open position and the closed position, the operation of high frequency pressure oscillation device 30 is not position sensitive. Also, the frequency of oscillation for the valve can be controlled and is not dependent on the rate of flow of gas generated by the patient.

As schematically shown in FIG. 1, actuating system 48 includes a control circuit 50 for providing a signal via line 52 to the actuating elements in valve assembly 46 that cause the valve to move to the open position or the closed position depending on the signal on line 52. A switch 54 is provided for turning the high frequency pressure oscillation device on and off. In an exemplary embodiment of the present invention, depressing switch 54 turns on the device, thereby actuating valve 46, and releasing switch 54 turns the system off. Thus, the device is only operational while switch 54 is depressed. A power supply 56 provides energy to control circuit 50 and to valve assembly 46. In the exemplary embodiment of the invention shown in FIG. 1, the rate at which the valve assembly opens and closes, i.e., blocks and unblocks path 44 between the patient and the source of breathing gas, is adjustable by means of an input device, which, in this embodiment, is a rotateable knob 58. Details of the control of the rate of oscillation are provided below with reference to FIG. 7.

It is to be understood that the present invention contemplates that any one of a variety of input devices can be used as on/off switch 54 and speed control input device 58. That is, on/off switch 54 and speed control input can be any input device capable of turning the high frequency pressure oscillation device on and off and adjusting the oscillation frequency of the valve, respectively. For example, a touch screen display, keypad, or a combination of the two can be used to input commands to the device.

Power supply 56 is any energy source that provides the appropriate type and level of energy to activate control circuit 50 and valve assembly 46. In a preferred embodiment of the present invention, power supply 56 is a rechargeable battery pack that selectively attaches to handle 34. When the battery drains below a predetermined level, as sensed by control circuit 50, a warning light or other alarm device actuates. The user is thus alerted to remove the battery pack for recharging. Of course, power supply 56 can be a conventional disposable battery or an AC power supply. In the latter case, an appropriate power converter or adapter may be necessary to provide DC power to control circuit 50 and valve assembly 46.

As shown in FIGS. 2–6B, valve assembly 46 includes a hollow, first or inner cylinder 60, which includes a center barrel 62, a first barrel 64 and a second barrel 66. First barrel 64 and second barrel 66 are coaxially positioned at opposite ends of center barrel 62. First cylinder 60 has an open first end 68, an open second end 70, a first slot 72 defined in a wall of second barrel 66 and third slots 74 defined in the wall of second barrel 66 between first slot 72 and second end 70. A separating plate 76 positioned in inner cylinder 60 and, more particularly, in second barrel 66, between first slot 72 and third slots 74 obstructs or prevents the flow of gas therebetween.

While the figures show first slot 72 as being two separate orifices in the wall of first cylinder 60, it is to be understood that the number of openings defining the first slot is not critical to the operation of the present invention so long as at least one slot is provided having a sufficient size so as to allow a substantially unobstructed flow of gas between the patient and the gas source (ambient atmosphere) when valve assembly 46 is in the open position. Similarly, third slots 74 can be one or more openings defined in the wall of first cylinder. In addition, the configuration for first slot 72 and third slot 74 can be other than that shown in the figures.

Figure 2:
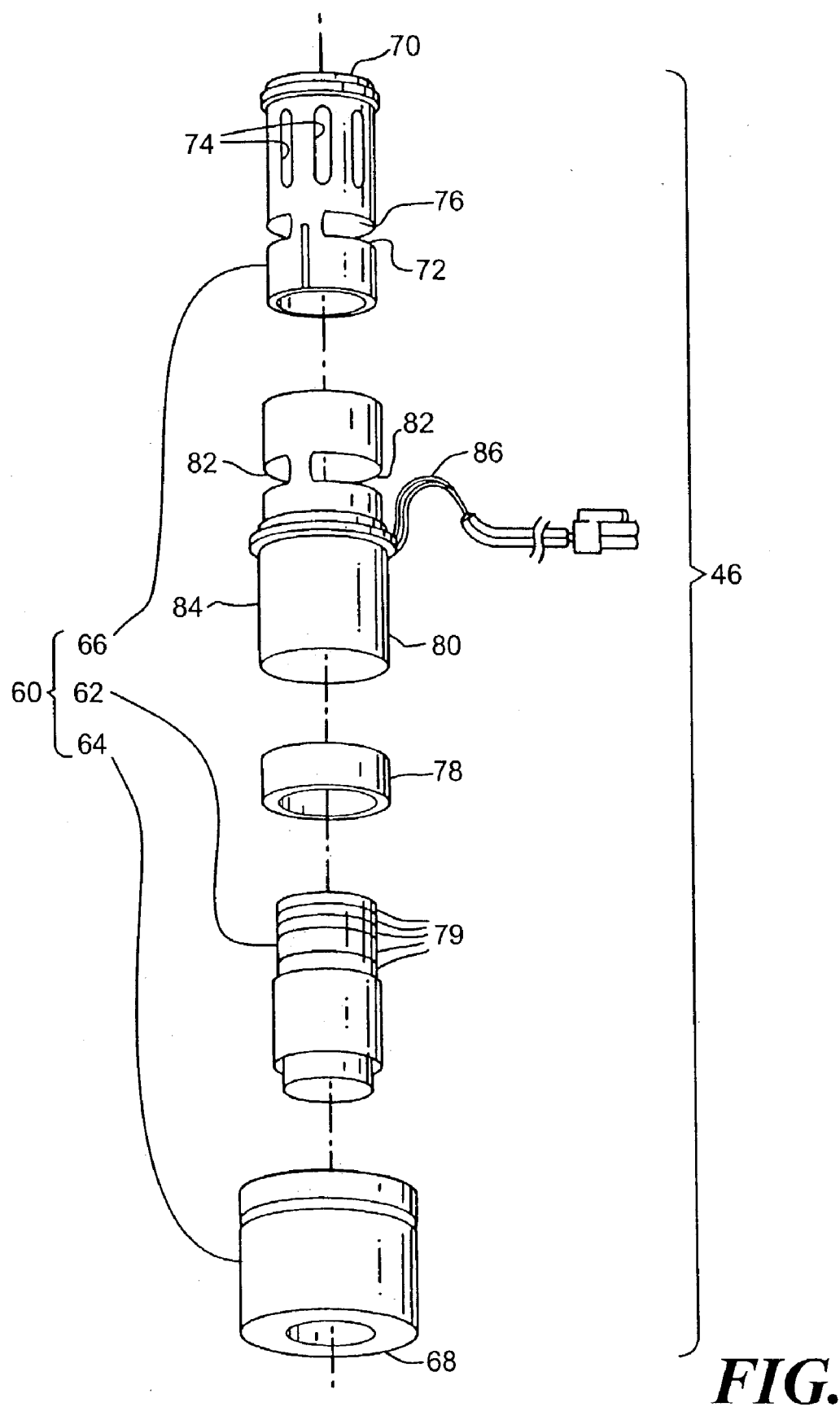
FIG. 2 is an exploded view illustrating the components of an exemplary embodiment of a sleeve valve used in the high frequency pressure oscillation device of FIG. 1.

In the illustrated exemplary embodiment, an annular permanent magnet 78 is secured around an end of center barrel 62 opposite first barrel 64. Preferably, magnet 78 is affixed to the exterior of center barrel 62. As shown in FIG. 2, the present invention contemplates providing grooves 79 in the center barrel to facilitate the attachment of these two members by serving as channels for holding glue or other adhesive. It is to be understood that other techniques for attaching the magnet to the center barrel are contemplated by the present invention. For example, magnet 78 can be threaded onto corresponding threads in the exterior surface of center barrel 72 or press fit onto the center barrel.

Valve assembly 46 also includes a second or outer cylinder 80 configured to be received around magnet 78 and first cylinder 60 and to move axially generally between first end 68 and second end 70 of first cylinder 60. Second cylinder 80 includes a second slot 82 defined in the wall thereof. In an assembled configuration, second slot 82 overlaps first slot 72 when in a open position, see FIGS. 6A and 6B, and does not overlap, i.e., blocks, first slot 72 when in a closed position, see FIGS. 5A and 5B.

A coil 84 is secured around outer cylinder 80 in magnetic flux coupled relation with magnet 78. Is should be noted that FIG. 4 illustrates a portion of second cylinder 80, with a portion of the coil shown in dashed lines. The present invention contemplates that coil 84 can be attached to the end of the portion of the second cylinder shown in FIG. 4 or can be wound around the outer cylinder as shown in FIGS. 5B and 6B. As shown in FIGS. 2, 5B, and 6B, a wire 86 extends from coil 84 for passing a current through the coil. Coil 84 is configured to receive DC current from control circuit 50.

According to one embodiment of the present invention, in response to receiving DC current of a first polarity, coil 84 urges second cylinder 80 axially relative to first cylinder 60 in a first direction indicated by arrow 88 in FIG. 6A. When displaced to the maximum amount possible in the first direction, second slot 82 in second cylinder 80 and first slot 72 in first cylinder 60 are aligned and valve assembly 46 is in an open position. FIGS. 6A and 6B illustrate second cylinder 80 displaced as far as possible in the first direction with second slot 82 and first slot 72 being generally aligned with one another so that gas can flow between open first end 68 and open second end 70, as indicated by arrow 90. In particular, gas flows from open first end 68 out of the aperture 92 defined by the overlap of second slot 82 and first slot 72 around the exterior of valve assembly 32 and back into an interior thereof, as indicated by arrows 93, via third slots 74. Gas then flows out of open end 70 to ambient atmosphere. Of course, gas can also flow in an opposite direction depending on whether the patient is inhaling or exhaling.

In response to receiving DC current of a second polarity, opposite the first polarity, coil 84 urges second cylinder 80 axially relative to first cylinder 60 in a second direction opposite the first direction as indicated by arrow 94 in FIG. 5A. When displaced to the maximum amount possible in the second direction, second slot 82 of second cylinder 80 obstructs first slot 72 of first cylinder 60 and valve 46 is in the closed position. As a result, gas entering open end 68, as indicated by arrow 96, does not flow through valve assembly 46.

While the present invention has been described above as using two polarities of DC current to energize coil 84 to move second cylinder 80 relative to first cylinder 60 in one of two longitudinal directions, it is to be understood that other techniques for moving the outer cylinder relative to the inner cylinder are contemplated by the present invention. For example, a spring or other similar mechanism can be used to urge second cylinder 80 in a first direction relative to first cylinder and a DC current through coil 84 can be used to urge the outer cylinder in an opposing direction. This configuration is advantageous in the only one polarity of current is required to be provided to coil 84.

As is the case with the first and third slots in the first cylinder, the size, shape and number of slots defining second slot 82 in second cylinder 80 can vary so long as the selectively blocking and unblocking of path 44 is accomplished as the second slot overlaps and does not overlap the first slot. In addition, while at least a portion of third slots 74 are at all time unblocked regardless of the position of the second cylinder relative to the first cylinder, the present invention contemplates that the second cylinder can be configured to block the third slots when valve assembly 46 is in the closed position.

Details of control circuit 50 according to one exemplary embodiment of the present invention are provided below with reference to FIG. 7. As noted above, control circuit 50 controls the supply of current to coil 84 in the valve assembly, and, thus, controls the opening and closing of path 44 between the patient and breathing gas source. In the illustrated embodiment, control circuit 50 includes a 555 timer 98 and a power amplifier 100 to provide bidirectional current through coil 84 in valve assembly 46. The frequency f at which the direction of current is altered is set by means of resistors R1 and R2 and capacitor C. It can be appreciated that in this embodiment, adjusting the frequency of oscillation for the valve also changes the duty cycle D. In the circuit shown in FIG. 7, the valve operating frequency f is given by:

$$f = \frac{1.44}{(R1 + 2R2)C} \text{ Hz,} \tag{1}$$

and the duty cycle D is given by:

$$D = \frac{R2}{R1 + 2R2} \%. \tag{2}$$

It can thus be appreciated that the values of R1, R2 and C can be adjusted to control the frequency and, hence, the duty cycle of the valve assembly. In an exemplary embodiment of the present invention, R1 and R2 are a 100 kΩ potentiometers and C is fixed at 10 μF. These ranges of values for R1, R2 and C allows for adjustment of the valve frequency between 1 and 25 Hz.

The bilevel output of 555 timer 98 is coupled to power amplifier 100, which is biased to a bias voltage X, which is greater than zero. As a result, when the voltage output from 555 timer 98 is high, i.e., greater than the bias voltage X, current flow through coil 84 in valve assembly 48 in a first direction. Conversely, when the voltage output from 555 timer 98 is low, i.e., less than the bias voltage X, current flow through coil 84 in valve assembly 48 in a second direction opposite the first direction. A high wattage resistor 102 is provided in series with valve assembly 46 to limit the current through coil 81.

Figure 7:
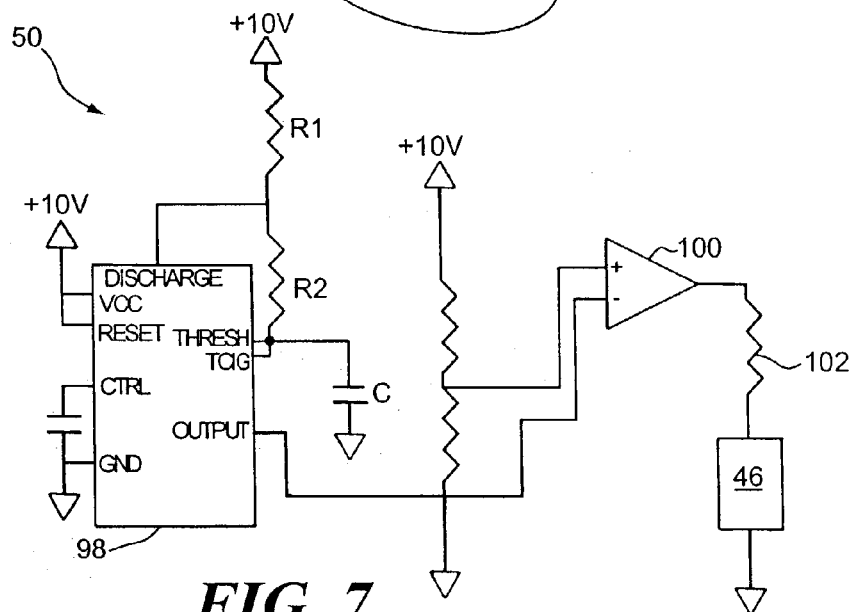
FIG. 7 is a schematic diagram of a control circuit used to operate the high frequency pressure oscillation device of FIG. 1.

It is to be understood that the circuit show in FIG. 7 and described above is one example of a suitable mechanism for controlling the actuation of the valve assembly. The present invention contemplates other techniques for controlling the valve assembly. For example, a suitably programmed microprocessor can be provided to provide an energizing signal to the valve assembly. It can be further appreciated that the frequency and duty cycle for the operation of the valve assembly can be controlled independently so that adjusting one does not necessarily affect the other. In a preferred embodiment of the present invention the duty cycle of the valve assembly is set at approximately 50%.

Figure 8:
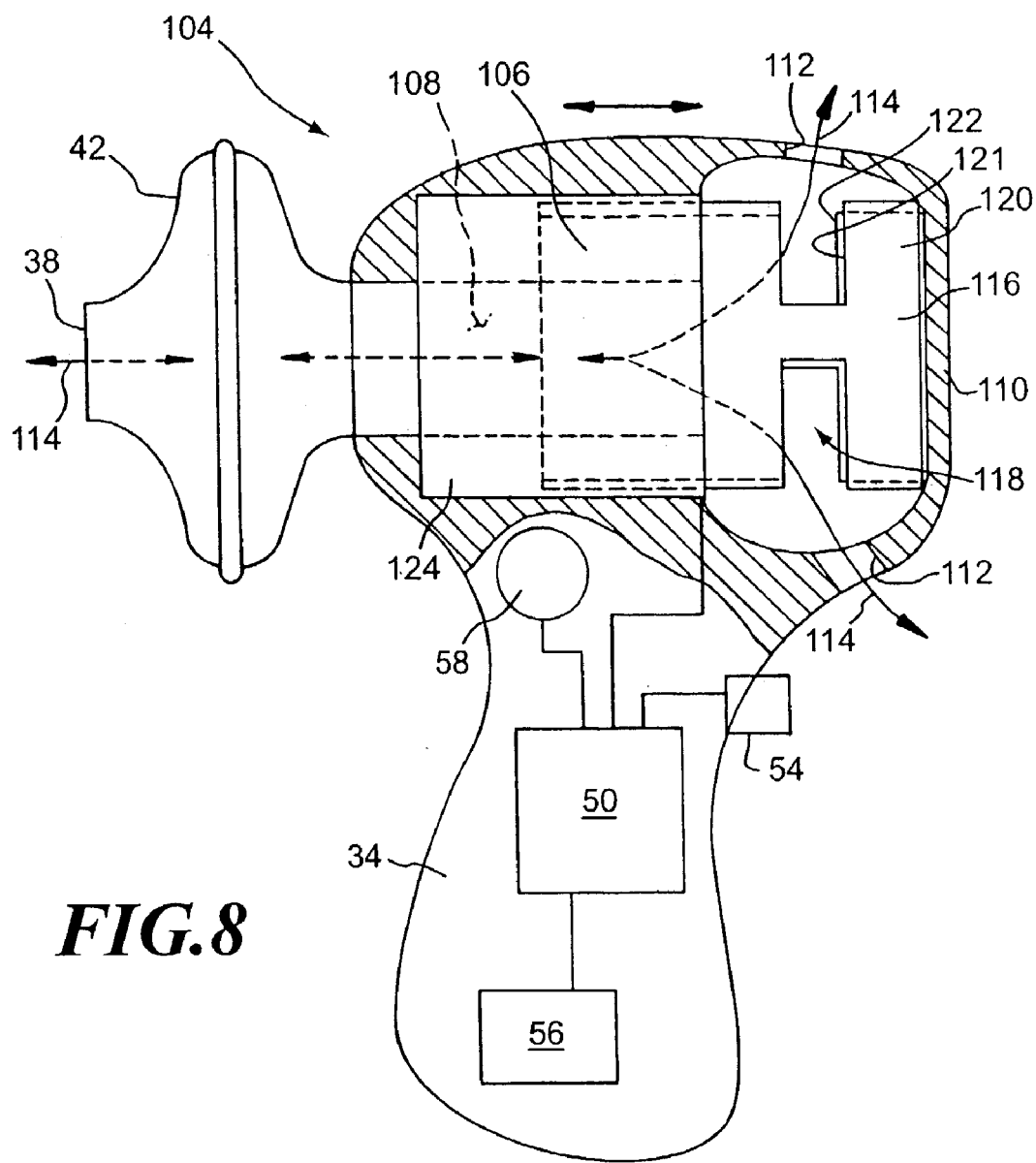
FIG. 8 is a side view, partially in section, of an alternative embodiment of a sleeve valve suitable for use with the high frequency pressure oscillation device of the present invention.

An alternative embodiment of a sleeve valve suitable for use with a high frequency pressure oscillation device 104 according to the principles of the present invention is described below with reference to FIG. 8, which is a side view, partially in section, of high frequency pressure oscillation device 104. Unlike the sleeve valve of FIGS. 1–6B, which includes third ports 74 and second open end 70 in the first cylinder to direct the flow of gas out the end of housing 32 opposite patient end 38, high frequency pressure oscillation device 104 includes a sleeve valve assembly 106 that does away with the third port and the need to redirect the flow of gas back into to first cylinder. Instead, gas entering a patient circuit 108 at patient end 38 is directed from valve assembly 106 when in the open position, as shown in FIG. 8, out of housing 10 via ports 112. Arrows 114 illustrate the path of gas flowing between patient end 38 and ports 112 through patient circuit 106. It is to be understood that the number, shape, size, and location of ports 112 can be varied to provide any desired flow path to atmosphere.

Most of the components of valve assembly 108 are the same as those of valve assembly 46. The primary difference between these two valves has to do with the shape of the second barrel in the first cylinder, and, in particular, with the elimination of the third ports in the second barrel, while first slots 72 remain unchanged. Second cylinder 116 of valve assembly 106 is substantially the same as second cylinder 80. In the open position shown in FIG. 8, a second slot 121 overlaps first slot 122 to define an aperture 118 through which gas is capable of flowing freely, thereby providing a substantially unobstructed path, as generally indicated by arrows 114, between the patient's airway and ambient atmosphere. In the closed position, an upper portion 120 of second cylinder 116 overlaps a first slot 122 defined in first cylinder 124 so that substantially no gas flows between the patient's airway and ambient atmosphere.

Figure 9:
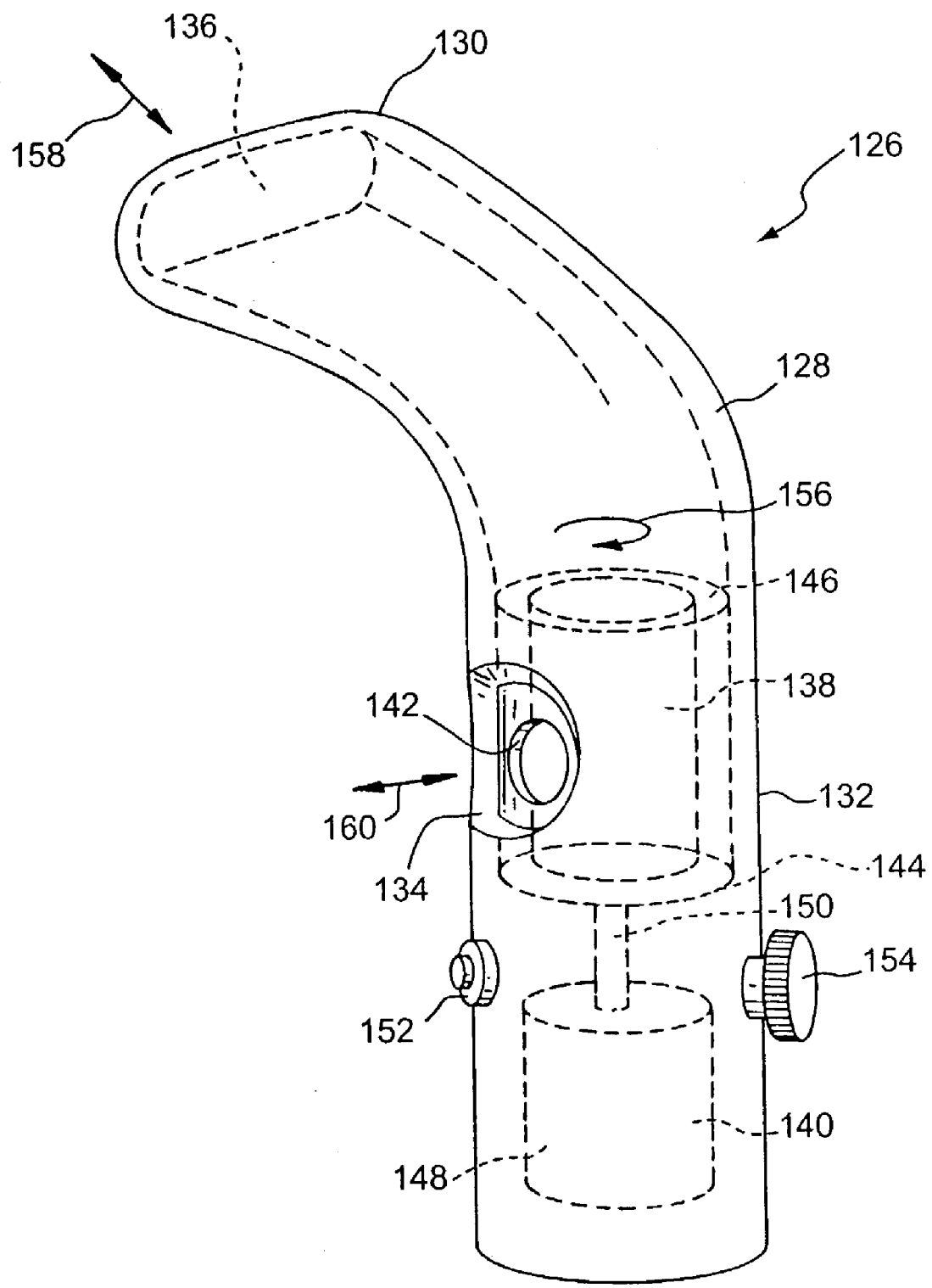
FIG. 9 is a perspective view of second embodiment of a high frequency pressure oscillation device according to the principles of the present invention.

FIG. 9 is a perspective view of second embodiment of a high frequency pressure oscillation device 126 according to the principles of the present invention. Device 126 includes a patient circuit 128, which, in the illustrated exemplary embodiment, is a generally cylindrical conduit having a mouthpiece end 130 and a breathing gas source coupling end 132. A first port 134 is defined in end 132 so that breathing gas can enter the patient circuit and exhaled gas can vent from the patient circuit. Likewise, a second port 136 is defined in mouthpiece end 130 so that the patient can deliver and receive gas from the source of breathing gas through the patient circuit. In the illustrated embodiment, the source of breathing gas is ambient atmosphere.

A valve 138 is disposed in patient circuit 128 at end 132 for selectively blocking and unblocking port 134. More specifically, valve 138 is disposed in patient circuit 128 so as to communicate the source of breathing gas with an airway of a patient when the valve is in a first position within the patient circuit, which corresponds to the position shown in FIG. 9. In addition, valve 138 blocks communication of the source of breathing gas with the patient's airway when the valve is in a second position within the patient circuit. Valve 138 moves between the first and second positions by being rotated a first direction by a rotating drive assembly 140.

In the illustrated exemplary embodiment, valve 138 is a generally cylindrical member having a hollow central cavity that extends along its longitudinal axis. A third port 142 is defined in a side wall of the valve to communicate the exterior of the valve with the central cavity. A first end 144 of valve 138 is closed while a second end 146 has an opening defined therein that also communicates an exterior of the valve with the central cavity. Valve 138 provides an unobstructed gas flow pathway from the source of breathing gas to the patient's airway when third port 142 overlaps first port 134, i.e., when valve 138 is in the first position. When third port 142 does not overlap first port 134, i.e., when valve 138 is in the second position, the pathway from the source of breathing gas to the patient's airway is obstructed, so that substantially no gas flows from the patient to the breathing gas source or vice versa.

In the exemplary embodiment illustrated in FIG. 9, rotating drive assembly 140 includes an electric motor 148 that generates a torque for rotating valve 138 and a mechanical linkage 150 in the form of a drive shaft that couples the motor to valve 138 such that the rotational force output by the motor rotates the valve. A power supply (not shown), which can be any type of power supply, such as batteries or an AC source, provides energy to motor 148 when the device is activated by an on/off button 152. Preferably, motor 148 is a variable speed motor so that the frequency at which the flow path between the patient and the gas source is interrupted can be controlled by means of a speed control knob 154 or any other type of input device.

To use high frequency pressure oscillation device 126, the user energizes motor 148 by actuating on/off button 152. Motor 148 rotates valve 138 in one direction, as indicated by arrow 156, so that valve 138 is alternatively placed in the first position, in which first port 134 and third port 142 overlap, and the second position, in which first port 134 and third port 142 do not overlap. As noted above, this rotational movement of valve 138 alternatively communicates the source of breathing gas with the patient's airway and blocks such communication.

The user breathes into mouthpiece end 130 so that a flow of gas is delivered to or received from the interior of patient circuit 128, as indicated by arrow 158, when valve 138 is in the first position. Gas is supplied to the interior of patient circuit 128 via ports 134 and 142 for consumption by the patient during inhalation or vented from the patient circuit during exhalation via the same port, as indicated by arrow 160, when valve 138 is in the first position. Because the free flow of gas between the patient and the gas source is periodically interrupted by valve 138 being in the second position, as the patient breathes into mouthpiece end 130, a series of pressure spikes occur in the patient's airway as a result of the temporary flow interruption caused by the closing of first port 134. These pressure spikes facilitate loosening and removal of the patient's airway secretions. A similar result occurs as the patient inhales through mouthpiece end 130, except that instead of abrupt increases in pressure being created, abrupt decreases of pressure are generated in the patient's airway.

It can be appreciated that a wide variety of configurations can be provided for patient circuit 128. For example, mouthpiece end 130 can be circular or oval, rather than the generally rectangular shape illustrated. In addition, the present invention contemplates providing a removeable mouthpiece that can be selectively detached from mouthpiece end 130 of patient circuit 128. Also, a bacteria filter can be provided at mouthpiece end 130.

It is to be further understood that more sophisticated control over the operation of the motor can be incorporated into the device. For example, the motor can be controlled so that its speed varies over the course of a treatment session. It should be noted that the specific components for controlling the motor and the interconnection of the input devices, i.e., on/off button 152 and speed control knob 154, are not illustrated in FIG. 9 for the sake of simplicity. It is believed that these components and interconnections would be well known to those skilled in the art.

Figure 10:
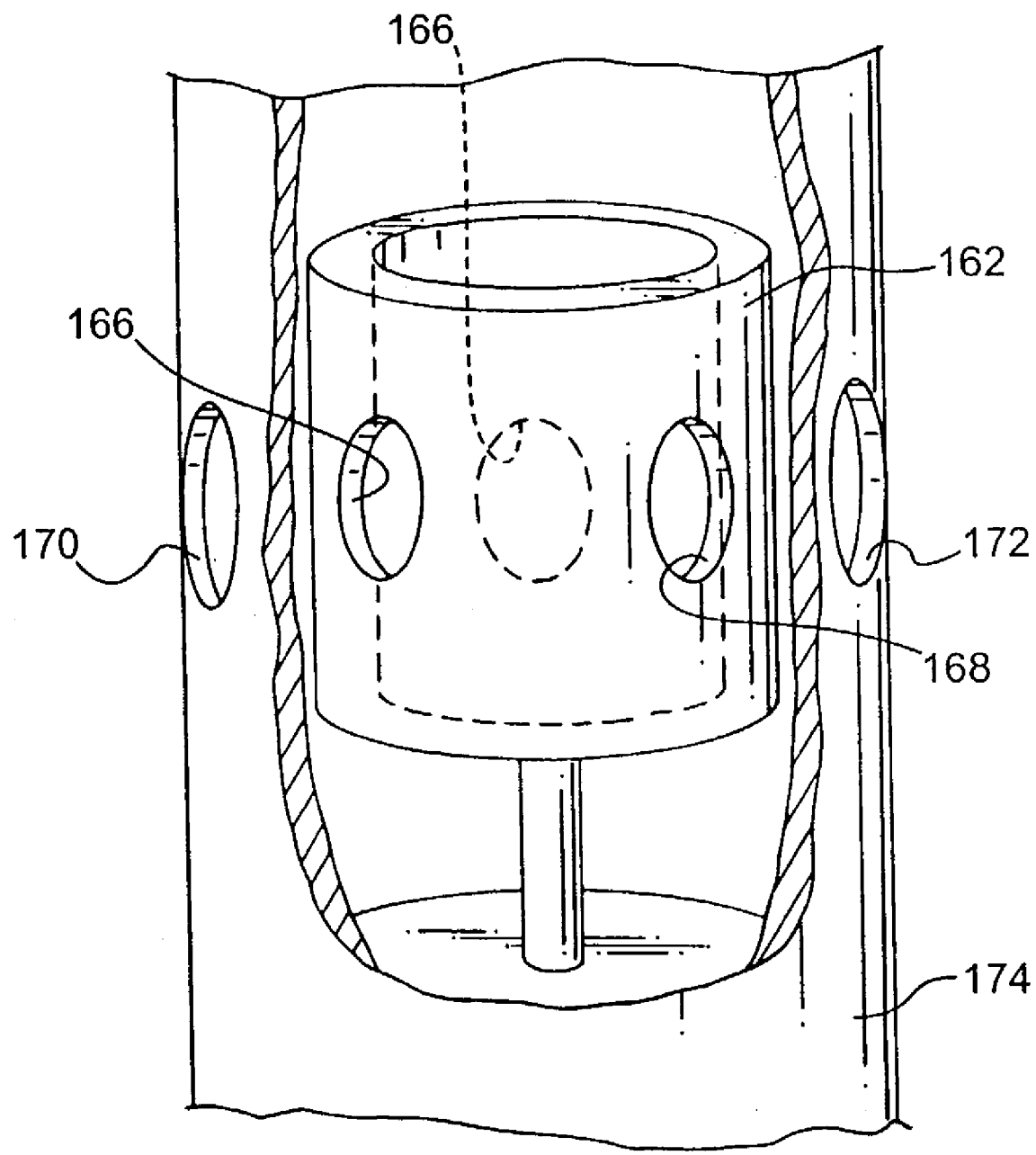
FIG. 10 is a perspective view illustrating an alternative embodiment of a rotary valve used in the high frequency pressure oscillation device of FIG. 9.

While FIG. 9 shows only one port in patient circuit 128 and valve 138, the present invention contemplates that more than one port can be provided in either or both of these components of device 126. For example, FIG. 10 illustrates a second exemplary embodiment of a rotary valve 162 that can be used in the high frequency pressure oscillation device of the present invention. In this embodiment, valve 162 includes a plurality of ports 164, 166, and 168 defined in the side wall of the valve, with all of the ports being aligned in generally the same circumferential location on the valve. In addition, FIG. 10 illustrates a plurality of ports 170 and 172 defined in patient circuit 174, with all of these ports also aligned in generally the same circumferential location on the patient circuit. It is to be understood, that multiple ports need not be provided in both the patient circuit and the rotary valve, as shown. On the contrary, the present invention contemplates providing multiple ports in only one of these components.

Those skilled in the art will appreciate that the number of ports, the shape or geometry of the ports, and the size of the ports can be varied so that a wide variety of pressure signals can be generated by the high frequency pressure oscillation device of the present invention when used by the patient. For example, the ports need not be circular, as shown, but can be rectangular, square, triangular or any other shape, so long as the cooperation of the ports in the valve and ports in the patient circuit serve to obstruct the free flow of gas between the patient and ambient atmosphere, either completely or partially, so that pressure oscillations are generated in the patient's airway.

It should be noted that valve 162 and patient circuit 174 are shown in FIG. 10 as being spaced apart from one another so that the ports in each can be clearly illustrated. Those skilled in the art understand that the functional high frequency pressure oscillation device should have a relatively small tolerance between these two components. Furthermore, FIG. 10 is believed to provide a clear illustration of the valve, including the opening defined in one of the axial surfaces of the valve that provides access to the central cavity defined in the valve. Valve 162 in FIG. 10 is substantially the same as valve 138 in FIG. 9 except for the number of ports defined in the side walls of the valve.

Figure 11:
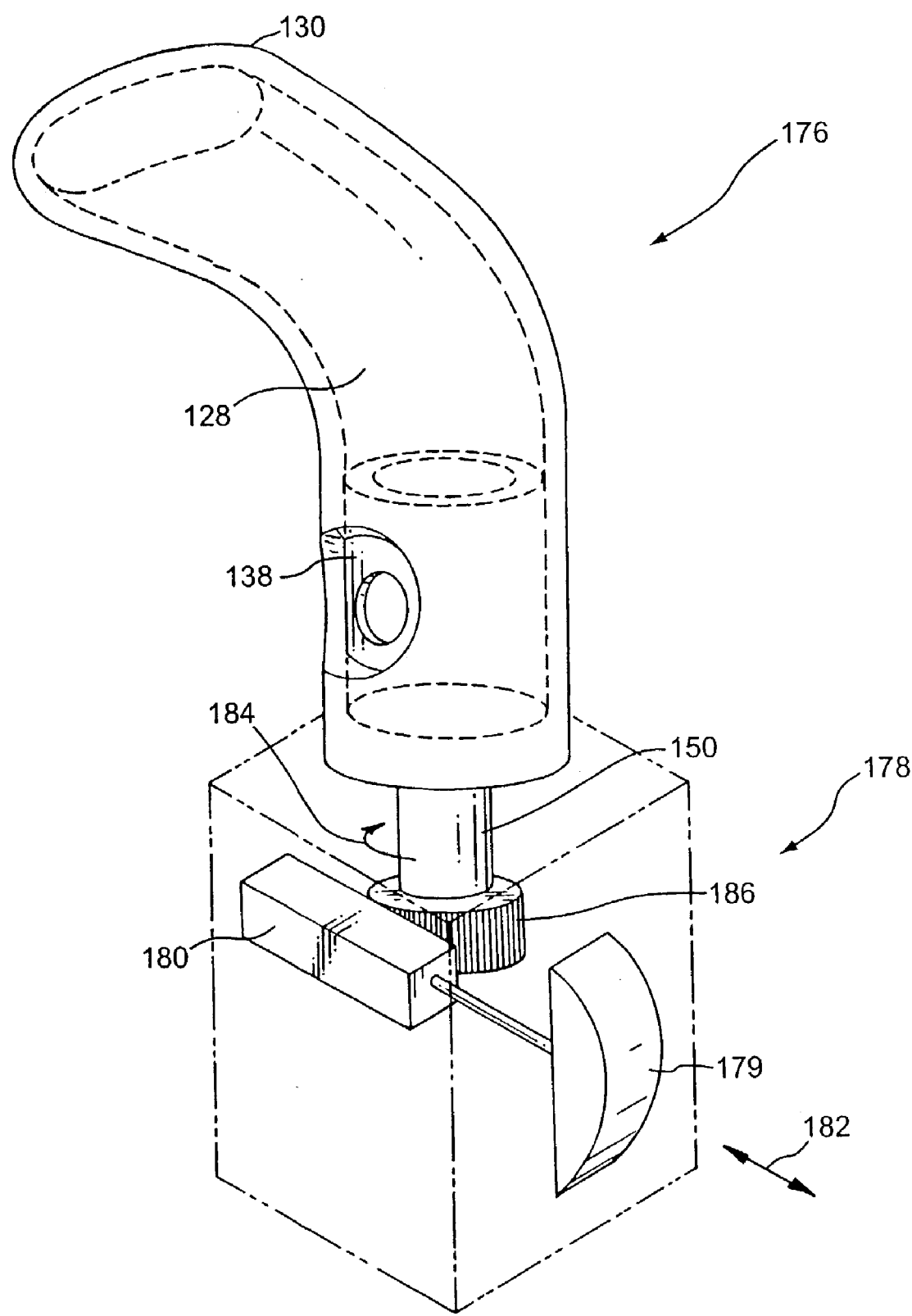
FIG. 11 is a perspective view of a high frequency pressure oscillation device according to a third embodiment of the present invention.

While FIG. 9 illustrates valve 138 as being rotated by an electric motor, the present invention contemplates other techniques that are not dependent on patient effort for imparting a rotational force on the valve to cause it so spin in one direction. One alternative technique for rotating the valve, other than using an electric motor, is shown in FIG. 11. High frequency pressure oscillation device 176 in FIG. 11 includes a manually operated system, generally indicated at 178, for rotating valve 138. This system includes a trigger 179 that is depressed by the user and a linkage 180 that moves laterally, as indicated by arrow 182, as a result of the trigger being depressed. Lateral movement of linkage 180 is translated into a rotational force, as indicated by arrow 184, by a gear 186 that engages linkage 180 as trigger 178 is depressed. This rotational force is translated to valve 138 via drive shaft 150. Preferably, a biasing mechanism (not shown) is provided in conjunction with linkage 180 to return the linkage and trigger 178 to their unactuated positions without affecting the rotation of shaft 150 so that the patient can repeatedly actuate trigger 178 to maintain the rotational movement of valve 138 while the patient breathes through patient circuit 128.

As noted above, the present invention contemplates that the high frequency pressure oscillation device can include one or more ports in the valve or patient circuit. The more ports in either of these components, the higher the frequency of pressure oscillations in the patient's airway, assuming the rotational speed remains constant. Of course, as the speed of rotation increases, the frequency of the pressure oscillations also increases.

Figure 12:
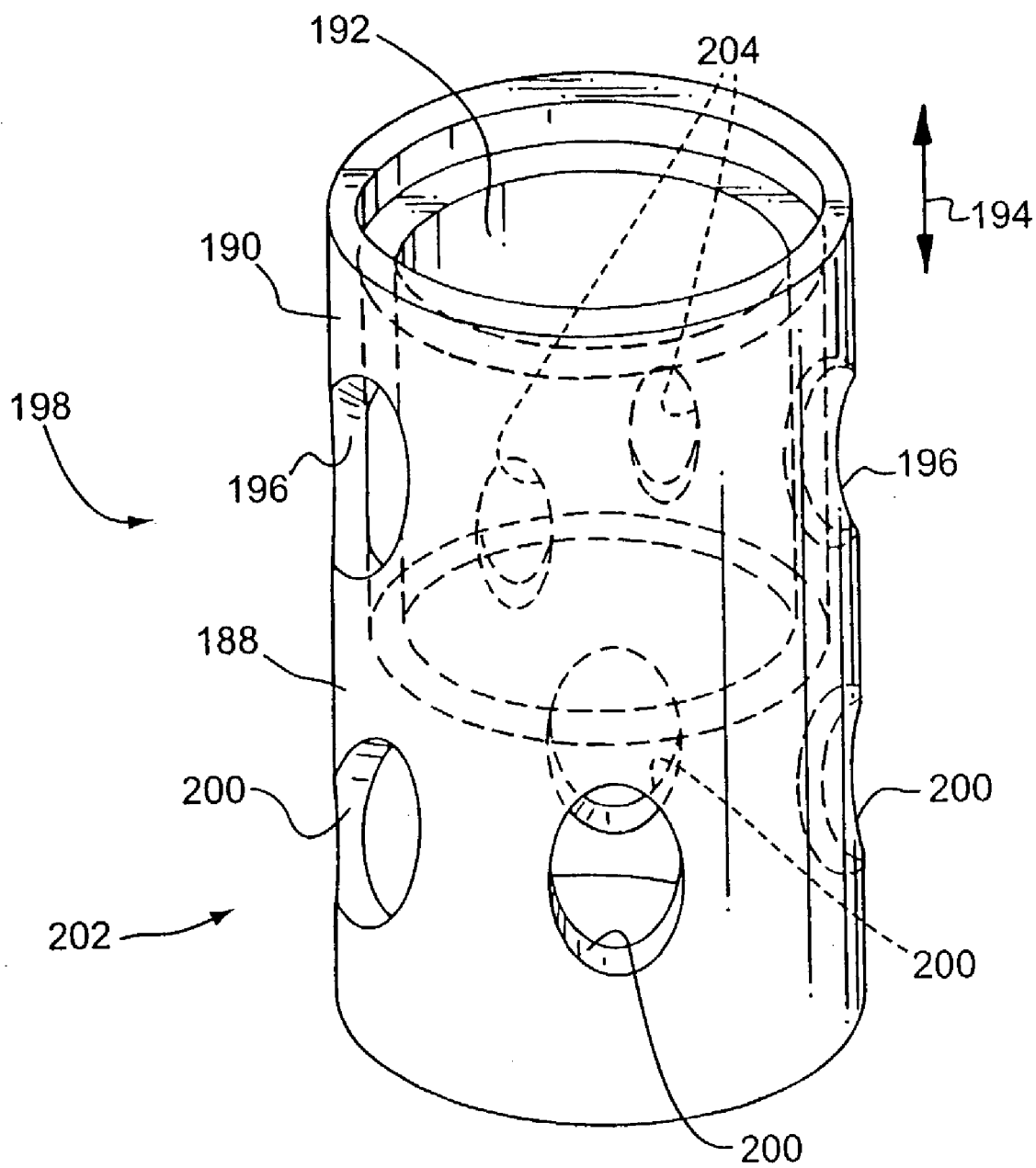
FIG. 12 is a perspective view illustrating a portion of a fourth embodiment of a high frequency pressure oscillation device of the present invention.

In the above embodiments, the range of frequencies for the pressure oscillations is limited by the range by which the speed of the motor can be varied. In addition, if the motor is a constant speed motor, the frequency of the pressure oscillations is also constant. FIG. 12, however, illustrates a further embodiment of a high frequency pressure oscillation device according to the principles of the present invention in which the frequency of the pressure oscillations can be varied independent of the motor speed. This is accomplished by providing the ability to change the number of ports in the patient circuit that align with the port of ports in the valve. It should be noted that FIG. 12 only illustrates a portion of the patient circuit.

As shown in FIG. 12, patient circuit 188 includes a conduit having a slideable portion 190 that moves axially relative to valve 192, as indicated by arrow 194. Slideable portion 190 includes a first number of ports 196 defined therein at a first circumferential location, generally indicated at 198, and a second number of ports 200 defined therein at a second circumferential location, generally indicated at 202. In the illustrated exemplary embodiment, two ports are provided at first circumferential location 198 and four ports are provided at second circumferential location 202. Ports 196 and 200 in the first and second circumferential locations 198 and 202, respectively, are capable of communicating an interior of patient circuit 188 to the breathing gas source when not blocked by valve 192.

The slideable portion is moveable in an axial direction relative to valve 192 so that in a first position, the first number of ports 196 at first circumferential location 198 are selectively blocked and unblocked by rotation of valve 192, while the second number of ports 200 at second circumferential location 202 remain blocked at all times during rotation of valve 192. FIG. 12 shows slideable portion 190 in this first position. When in a second position (not shown), the second number of ports 200 at the second circumferential location 202 are selectively blocked and unblocked by rotation of valve 192 and the first number of ports 196 at first circumferential location 198 are blocked at all times during rotation of valve 192. By selecting which set of ports are to be selectively unblocked by moving slideable portion 190 so that the desired set of ports is aligned with the ports in valve 192, the device of FIG. 12 allows the user to choose or adjust the frequency of the pressure oscillations.

Valve 192 in FIG. 12 includes two ports 204 for selectively unblocking ports 196 or 200 as it rotates within patient circuit 188. It is to be understood, however, that the number, shape and size of the port or ports in valve 192 can be different from that shown. Similarly, the number shape and size of the ports at the first and second circumferential locations in the patient circuit can also be different from that shown. In addition, further sets of ports at other circumferential locations can be provided in the patient circuit so that additional variations in the frequency of the pressure oscillations are possible.

Although the embodiment of the present invention described above and shown in FIGS. 1–12 interrupts the free flow of gas between the patient and the gas source during both the inspiratory and expiratory phases of the patient's breathing cycle, it is to be understood that the present invention contemplates interrupting the free flow of gas between the patient and the gas source only during one of these phases of the breathing cycle. For example, in one embodiment of the present invention, at all times during the inspiratory phase, the path between the patient and the gas source remain unobstructed and, during the inspiratory phase, the path between the patient and the gas source is at least partially unobstructed by the rotary valve.

For the sleeve valve of FIGS. 1–6B this can be accomplished by oscillating the sleeve valve only during exhalation, while placing the valve in the open position during inspiration. In which case, flow direction sensing elements are necessary to differentiate between inspiration expiration.

In another embodiment, a one-way valve is provided in the patient circuit to ensure that gas flows freely to the patient during the inspiratory phase, i.e., does not flow through the rotating valve or the sleeve valve. During exhalation, however, the one-way valve operates to direct the flow of gas from the patient through the rotating valve or sleeve valve.

In yet another embodiment with respect to the rotating valve, the present invention contemplates operating the rotating valve such that during the inspiratory phase, the ports in the rotary valve and the ports in the patient circuit remain overlapped, thereby providing a substantially unobstructed path between the patient and the gas source. During the expiratory phase, the rotating valve obstructs this free flow of gas. However, in addition to requiring a flow sensing capability to differentiate between inspiration and expiration, this embodiment of the present invention requires stopping and starting the rotating valve rather abruptly.

In the above-described embodiments, valves 46, 138, 162, and 192 substantially block the pathway from the source of breathing gas to the patient's airway when in the second or closed position to create the desired pressure spikes. It is to be understood, however, that the present invention contemplates configuring the valve so that in the second or closed position, the valve does not completely block this pathway; rather it provides an increase in the restriction to flow through the path. This abrupt increase in the restriction to flow between the patient's airway and the source of breathing gas, even though not a complete blockage, will also create pressure spikes that, in many cases, are sufficient to assist in secretion clearance. This is accomplished in sleeve valve assembly 46 by preventing a complete overlap between first port 72 and second port 82 in the closed position. This is accomplished in the rotating valve embodiments shown in FIGS. 9–12 by modifying the size and shape of the ports in the rotating valve and/or by modifying the size and shape of porting in the patient circuit so that there is always at least a small flow of gas between the patient's airway and the gas source.

Restricting the flow of gas between the patient and the gas source, rather than completely blocking it, can also be accomplished in either embodiment of the present invention by providing a constant leak of gas between the patient and the gas source. For example, in the embodiment shown in FIGS. 1 and 8, a constant leak can be achieved by providing a clearance between the first barrel 66 of first cylinder 60 and second cylinder 80. In the embodiments shown in FIGS. 9–12, a constant leak can be provided by providing a clearance between the patient circuit and the rotating valve.

Figure 13:
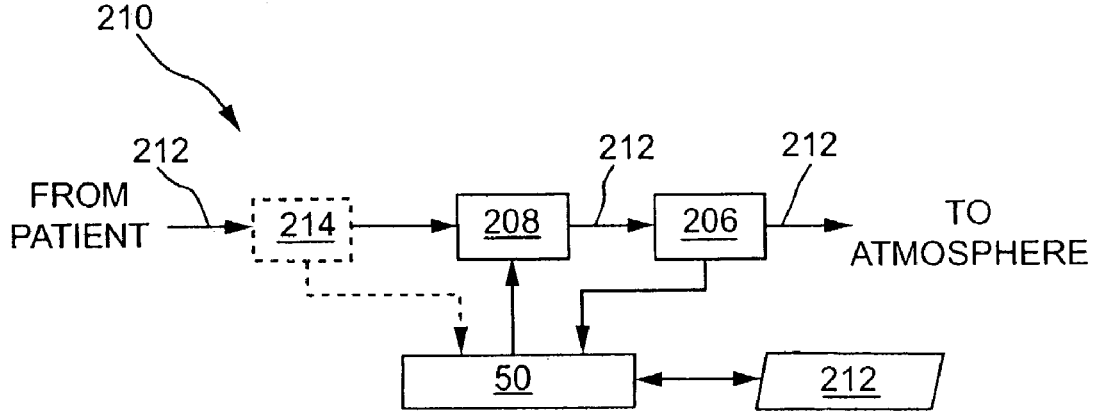
FIG. 13 is a schematic diagram illustrating a fifth embodiment of a high frequency pressure oscillation device in combination with a spirometer according to the principles of the present invention.

The present invention also contemplates that the above described high frequency pressure oscillation devices can be used in combination with a spirometer, which typically includes a flow meter, so that the data regarding the pulmonary function of the patient, such as the flow or pressure of the gas to or from the patient, can be accumulated while the pressure oscillations take place. In addition, by providing a flow sensor in the patient circuit, the device can be used as either a high frequency pressure oscillation device or as a spirometer, thereby incorporating the features of two dissimilar devices into a single unit. FIG. 13 is a schematic diagram illustrating one embodiment demonstrating how the features of a spirometer, namely, a flow meter 206, can be incorporated with the features of a high frequency pressure oscillation device, namely, a flow restricting valve 208 to provide a combination spirometer/high frequency pressure oscillation device 210.

As shown in FIG. 13, flow sensor 206 is provided in the patient circuit, as generally indicated by arrows 212, so that gas exiting valve 208 during patient exhalation passes through the flow sensor. It is to be understood, that the present invention also contemplates providing a flow sensor 214 (shown in dashed lines in FIG. 13) on the other side of valve 208 instead of or in addition to flow sensor 206. Valve 208 corresponds to any of the above described valves for periodically restricting the flow of gas between the patient's airway and the source of breathing gas, such as valve assembly 46 in FIGS. 1–6B, valve 106 in FIG. 8, valve 138 in FIG. 9, valve 162 in FIG. 10, valve 192 in FIG. 12. In addition, flow sensors 206 and 214 are any conventional device that is capable of measuring the flow of gas. For example, a typically flow sensor includes two pressure ports located on either side of a flow restricting element to measure the pressure drop induced by the flow restricting element.

It is to be understood that the present invention also contemplates measuring the pressure of gas within patient circuit 212 at any location to determine additional information, such as information regarding pressure variations in the patient's airway as a result of the periodic restrictions to flow imposed by valve 208.

The present invention contemplates providing the flow or pressure sensor or sensors within the housing containing the patient circuit and the control valve, with the user selecting whether the pressure oscillation feature, the spirometer feature, or both are operated. Preferably, an input/output device 216 is provided that includes a mode selecting capability, such as a switch or dial, allowing the user to select whether the device operates in the pressure oscillation mode of the spirometer mode. When in the pressure oscillation mode, the user can further select whether or not the flow or pressure sensors are operating to collect data while the pressure oscillations are being created.

The present invention also contemplates that the flow and/or pressure sensors are provided a modular component that attaches to either end of the patient circuit. In which case, operating the device as a spirometer merely involves attaching the modular flow sensor system and breathing into the device, as done with a conventional spirometer, without actuating the pressure oscillation system. In one embodiment, a communication port is provided on the housing of the pressure oscillation device so that data from the flow sensor, the pressure sensor, or both can be provided to control unit 50.

Including a flow sensor, a pressure sensor, or one or more of both of these sensors in the patient circuit provides at least two functions. In one mode of operation, these sensors collect data during operation of the pressure oscillation device. This data can include the patient's breathing rate, tidal volume, flow rate, level of the pressure spikes, changes in flow as a result of the flow restrictions, volume of displaced air, and any other pulmonary information associated with the flow of gas to the patient or the pressure oscillations generated by the periodic restriction to flow produced by the valve. In this embodiment, an input/output device 216 displays the collected data and is used to provide commands, such as requests for data, to the control circuit that controls the collection, processing, and display of the data.

The data collected by the flow and/or pressure sensors can be recorded or output to monitor the condition of the patient or the operation of the device. However, the present invention also contemplates controlling the operation of the pressure oscillation device, such as the oscillation frequency, duty cycle, the amount of flow restriction provided by flow restricting valve 208, or any combination thereof, based on the information collected by the sensing devices. For example, the rate of oscillation can be increased as the flow through the device increases and the rate of oscillation can be decreased as the flow rate decreases, or vice versa. In addition, the degree by which the flow is restricted can be increased as the flow rate decreases. In short, the pressure oscillations can be controlled in any manner that enhances the secretion clearance capabilities of the present invention.

In another mode of operation, these sensors, and, in particular, the flow sensor, allows the device of the present invention to function as a conventional spirometer, providing all of the data collection, processing, storing, and transmission capabilities found therein. In this spirometer mode of operation, valve 208 is placed in the open position and is maintained in that position during operation of the device in the spirometer mode so that there is substantially no restriction to flow as the patient uses the device as a spirometer.

As a spirometer, the device of the present invention is capable of being used in the same manner as a conventional spirometer, e.g., determine the flow and volume of gas exhaled and inhaled during a forced expiratory maneuver. This information is typically plotted in a volume-time curve or a flow-volume loop and is used to measure, determine or calculate characteristics of the patient associated with his or her pulmonary function. Spirometers are also used to determine a patient's patient peak expiratory flow (PEF), forced expiration volume ($FEV_1$), $FEF_{25-75}$, FVC, and the $FEV_1$/FVC ratio. Input/output device 216 can be used to display, download, or communicate this information to a user, either at the spirometer itself or at a remote location via a communication link or data transfer device.

As noted above, the present invention also contemplates sensing and collecting data concerning the operation of the device. Such data includes the oscillation frequency or average oscillation frequency set by the user during each use, the amount of time the device is operated, the number of times a day the unit is used, the time of day it is used, or any combination of these items. To monitor time of use, the control circuit would include a timer that increments during use or a clock that indicates the time periods when the device is operated. This information may be helpful, for example, in monitoring the condition of a patient on an on-going basis and patient compliance.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A high frequency pressure oscillation device comprising:
   a patient circuit defining a closed path between a single source of breathing gas and an airway of a patient;

a valve disposed in the patient circuit such that in an open position the path between such a source of breathing gas and an airway of a patient is substantially unobstructed, and, in a closed position, the path between such a source of breathing gas and an airway of a patient is at least partially obstructed;

an actuating system associated with the valve that alternatively places the valve in the open position and the closed position at a predetermined oscillation rate independent of patient effort, wherein the valve is disposed in the patient circuit and configured such that rotating the valve in a first direction alternatively places the valve in the open position and the closed position, and wherein the actuating system comprises a rotating drive assembly operatively coupled to the valve to rotate the valve in the first direction; and a pulmonary measurement means associated with the patient circuit that measures a characteristic associated with a pulmonary function of a patient, wherein the device includes a secretion clearance mode and a spirometer mode.

2. A device according to claim 1, wherein the pulmonary measurement means is a flow sensor that measures a rate of flow of gas through the patient circuit.

3. A device according to claim 2, further comprising:

a control unit, receiving an output of the flow sensor to determine a pulmonary characteristic of such a patient based on the output of the flow sensor; and an output device providing a human perceivable indication of such a pulmonary characteristic of a patient.

4. A high frequency pressure oscillation device according to claim 1, wherein the patient circuit includes a conduit having a plurality of breathing gas openings defined therein communicating an interior of the conduit to the breathing gas source and a patient end opening defined therein communicating the interior of the conduit with an airway of a patient, wherein the valve is disposed in the conduit such that the valve blocks the plurality of breathing gas openings responsive to the valve being in the closed position and unblocks at least one of the breathing gas openings responsive to the valve being in the open position.

5. A high frequency pressure oscillation device according to claim 1, wherein the patient circuit includes a conduit having a slideable portion, the slideable portion having a first number of breathing gas openings defined therein at a first circumferential location and a second number of breathing gas openings defined therein at a second circumferential location, wherein the breathing gas openings in the first and the second circumferential locations communicate an interior of the conduit to the breathing gas source, wherein the conduit also has a patient end opening defined therein communicating the interior of the conduit with an airway of a patient, and wherein the slideable portion is moveable in an axial direction relative to the valve so that in a first position the first number of breathing gas openings are selectively blocked and unblocked by rotation of the valve and the second number of breathing gas openings are blocked and in a second position the second number of breathing gas openings are selectively blocked and unblocked by rotation of the valve and the first number of breathing gas openings are blocked.

6. A high frequency pressure oscillation device according to claim 1, wherein the rotating drive assembly includes:

a power supply;

an electric motor operatively coupled to the power supply, the motor having an output shaft that rotates responsive to energy being provided to the motor by the power supply; and a mechanical linkage coupling the motor to the valve such that a torque output by the motor rotates the valve.

7. A high frequency pressure oscillation device according to claim 6, further comprising an input device operatively coupled to the motor, wherein the motor is a variable speed motor, and wherein a speed of rotation of the output shaft is controlled via the input device.

8. A high frequency pressure oscillation device comprising:

conduit means for coupling a single source of breathing gas with an airway of a patient via a closed path;

flow controlling means for controlling a flow of gas in the conduit means by substantially unblocking the path responsive to the flow control means being in an open position and at least partially obstructing the path responsive to the flow controlling means being in a closed position;

actuating means for alternatively placing the flow controlling means in the open position and the closed position at a predetermined oscillation rate independent of patient effort, wherein the flow controlling means comprises a valve is disposed in the conduit means and configured such that rotating the valve in a first direction alternatively places the valve in the open position and the closed position within the conduit means, and wherein the actuating means comprises means for rotating the valve in the first direction; and a pulmonary measurement means associated with the conduit means that measures a characteristic associated with a pulmonary function of a patient.

9. A device according to claim 8, wherein the pulmonary measurement means is a flow sensor that measures a rate of flow of gas through the conduit means.

10. A device according to claim 9, further comprising:

a control unit, receiving an output of the flow sensor to determine a pulmonary characteristic of such a patient based on the output of the flow sensor; and an output device providing a human perceivable indication of such a pulmonary characteristic of a patient.

11. A method of providing high frequency pressure oscillations in an airway of a patient comprising:

a) providing a patient circuit defining a closed path between a single source of breathing gas and an airway of a patient;

b) providing a valve in the patient circuit adapted to control a flow of gas in the closed path;

c) moving the valve to an open position within the patient circuit to substantially open the path between a source of breathing gas and an airway of a patient;

d) moving the valve to a closed position within the patient circuit to substantially restrict the path between such a source of breathing gas and an airway of a patient, wherein moving the valve between the open position and the closed position is accomplished independent of patient effort;

e) repeating steps c) and d) to alternatively place the valve in the open and the closed positions at a predetermined oscillation rate, wherein moving the valve to the open and closed positions includes rotating the valve in a first direction within the patient circuit; and measuring a characteristic associated with a pulmonary function of a patient.

12. A method according to claim 11, wherein measuring a characteristic associated with a pulmonary function of a patient includes measuring a rate of flow of gas through the patient circuit.

13. A high frequency pressure oscillation device comprising:
 a patient circuit defining a closed path between a source of breathing gas and an airway of a patient;
 a valve disposed in the patient circuit such that in an open position the path between such a source of breathing gas and an airway of a patient is substantially unobstructed, and, in a closed position, the path between such a source of breathing gas and an airway of a patient is at least partially obstructed;
 an actuating system associated with the valve that alternatively places the valve in the open position and the closed position at a predetermined oscillation rate independent of patient effort, wherein the valve is disposed in the patient circuit and configured such that rotating the valve in a first direction alternatively places the valve in the open position and the closed position, and wherein the actuating system comprises a rotating drive assembly operatively coupled to the valve to rotate the valve in the first direction;
 a pulmonary measurement means associated with the patient circuit that measures a characteristic associated with a pulmonary function of a patient;
 wherein the patient circuit includes a conduit having a first opening defined therein communicating an interior of the conduit to such a source of breathing gas and a second opening defined therein communicating the interior of the conduit with an airway of a patient;
 wherein the valve is a generally cylindrical member having a hollow central cavity defined therein extending along a longitudinal axis of the cylindrical member, the cylindrical member having a third opening defined in a side wall thereof communicating an exterior of the cylindrical member with the central cavity and a fourth opening defined on a first axial surface of the cylindrical member that also communicates an exterior of the cylindrical member with the central cavity; and
 wherein the valve provides an unobstructed path between a source of breathing gas and an airway of a patient responsive to the third opening overlapping the first opening, and substantially blocks the path responsive to the third opening not overlapping the first opening.

14. A high frequency pressure oscillation device comprising:
 a patient circuit defining a closed path between a source of breathing gas and an airway of a patient;
 a valve disposed in the patient circuit such that in an open position the path between such a source of breathing gas and an airway of a patient is substantially unobstructed, and, in a closed position, the path between such a source of breathing gas and an airway of a patient is at least partially obstructed;
 an actuating system associated with the valve that alternatively places the valve in the open position and the closed position at a predetermined oscillation rate independent of patient effort, wherein the valve is disposed in the patient circuit and configured such that rotating the valve in a first direction alternatively places the valve in the open position and the closed position, and wherein the actuating system comprises a rotating drive assembly operatively coupled to the valve to rotate the valve in the first direction;
 a pulmonary measurement means associated with the patient circuit that measures a characteristic associated with a pulmonary function of a patient;
 wherein the patient circuit includes a conduit having a first opening defined therein communicating an interior of the conduit to such a source of breathing gas and a second opening defined therein communicating the interior of the conduit with an airway of a patient;
 wherein the valve is a generally cylindrical member having a hollow central cavity defined therein extending along a longitudinal axis of the cylindrical member, the cylindrical member having a third opening defined on a first axial surface of the cylindrical member communicating an exterior of the cylindrical member with the central cavity and having a plurality of side wall openings defined in a side wall thereof communicating an exterior of the cylindrical member with the central cavity; and
 wherein the valve provides an unobstructed path between a source of breathing gas and an airway of a patient responsive to one of the plurality of side wall openings overlapping the first opening and substantially blocks the path responsive to the side wall openings not overlapping the first opening.

15. A high frequency pressure oscillation device comprising:
 a patient circuit defining a closed path between a source of breathing gas and an airway of a patient;
 a valve disposed in the patient circuit such that in an open position the path between such a source of breathing gas and an airway of a patient is substantially unobstructed, and, in a closed position, the path between such a source of breathing gas and an airway of a patient is at least partially obstructed;
 an actuating system associated with the valve that alternatively places the valve in the open position and the closed position at a predetermined oscillation rate independent of patient effort, wherein the valve is disposed in the patient circuit and configured such that rotating the valve in a first direction alternatively places the valve in the open position and the closed position, and wherein the actuating system comprises a rotating drive assembly operatively coupled to the valve to rotate the valve in the first direction;
 a pulmonary measurement means associated with the patient circuit that measures a characteristic associated with a pulmonary function of a patient; and
 wherein the valve is a generally cylindrical member having a hollow central cavity defined therein extending along a longitudinal axis of the cylindrical member, the cylindrical member having a first number of openings defined in a side wall at a first circumferential location thereof communicating an exterior of the cylindrical member with the central cavity, a second number of openings defined in the side wall also communicating the exterior of the cylindrical member with the central cavity at a second circumferential location, and a third opening defined on a first axial surface of the cylindrical member that communicates the exterior of the cylindrical member with the central cavity.

16. A high frequency pressure oscillation device comprising:
- a patient circuit defining a closed path between a source of breathing gas and an airway of a patient;
- a valve disposed in the patient circuit such that in an open position the path between such a source of breathing gas and an airway of a patient is substantially unobstructed, and, in a closed position, the path between such a source of breathing gas and an airway of a patient is at least partially obstructed;
- an actuating system associated with the valve that alternatively places the valve in the open position and the closed position at a predetermined oscillation rate independent of patient effort, wherein the valve is disposed in the patient circuit and configured such that rotating the valve in a first direction alternatively places the valve in the open position and the closed position, and wherein the actuating system comprises a rotating drive assembly operatively coupled to the valve to rotate the valve in the first direction; and
- a pulmonary measurement means associated with the patient circuit that measures a characteristic associated with a pulmonary function of a patient; and
- wherein the rotating drive assembly includes:
  - a mechanical linkage operatively coupled to the valve;
  - a manually actuated member adapted to receive a force imparted by a user; and
  - a mechanism operatively coupled to the manually actuating member for altering the force on the manually actuated member into a rotational force and for providing the rotational to the mechanical linkage.

17. A high frequency pressure oscillation device comprising:
- a patient circuit defining a closed path between a source of breathing gas and an airway of a patient;
- a valve disposed in the patient circuit such that in an open position the path between such a source of breathing gas and an airway of a patient is substantially unobstructed, and, in a closed position, the path between such a source of breathing gas and an airway of a patient is at least partially obstructed;
- an actuating system associated with the valve that alternatively places the valve in the open position and the closed position at a predetermined oscillation rate independent of patient effort, wherein the valve is disposed in the patient circuit and configured such that rotating the valve in a first direction alternatively places the valve in the open position and the closed position, and wherein the actuating system comprises a rotating drive assembly operatively coupled to the valve to rotate the valve in the first direction; and
- a pulmonary measurement means associated with the patient circuit that measures a characteristic associated with a pulmonary function of a patient; and
- a mode selection switch that allows a user to select between at least the following two modes of operation: (1) a secretion clearance mode in which the actuating means alternatively places the valve in the open position and the closed position at a predetermined oscillation rate, and (2) a spirometer mode in which the valve remains in the open position and the pulmonary measurement means measures a characteristic associated with a pulmonary function of a patient.

18. A high frequency pressure oscillation device comprising:
- a patient circuit defining a closed path between a source of breathing gas and an airway of a patient;
- a valve disposed in the patient circuit such that in an open position the path between such a source of breathing gas and an airway of a patient is substantially unobstructed, and, in a closed position, the path between such a source of breathing gas and an airway of a patient is at least partially obstructed;
- an actuating system associated with the valve that alternatively places the valve in the open position and the closed position at a predetermined oscillation rate independent of patient effort, wherein the valve is disposed in the patient circuit and configured such that rotating the valve in a first direction alternatively places the valve in the open position and the closed position, and wherein the actuating system comprises a rotating drive assembly operatively coupled to the valve to rotate the valve in the first direction; and
- a pulmonary measurement means associated with the patient circuit that measures a characteristic associated with a pulmonary function of a patient; and
- a mode selection switch that allows a user to select between at least the following two modes of operation: (1) a secretion clearance mode in which the actuating means alternatively places the flow controlling means in the open position and the closed position at a predetermined oscillation rate, and (2) a spirometer mode in which the flow controlling means remains in the open position and the pulmonary measurement means measures a characteristic associated with a pulmonary function of a patient.

* * * * *